United States Patent [19]

Baron

[11] Patent Number: 4,788,007

[45] Date of Patent: Nov. 29, 1988

[54] OPHTHALMIC U.V. ABSORPTIVE EMOLLIENT

[76] Inventor: Neville A. Baron, 146 Sanpiper Key, Secaucus, N.J. 07094

[21] Appl. No.: 935,838

[22] Filed: Nov. 28, 1986

[51] Int. Cl.[4] .................... F21V 9/06

[52] U.S. Cl. .................... 252/589; 424/195.1; 514/912; 514/944

[58] Field of Search .................... 424/195.1; 514/912, 514/944, 954; 252/582, 588, 589

[56] References Cited

U.S. PATENT DOCUMENTS

| | | | |
|---|---|---|---|
| 3,878,197 | 4/1975 | Maret | 260/236.5 |
| 4,248,861 | 2/1981 | Schutt | 424/92 |
| 4,407,792 | 10/1983 | Schoenwald et al. | 424/81 |
| 4,465,629 | 8/1984 | Maughan | 424/195.1 |
| 4,481,185 | 11/1984 | Grollier et al. | 514/938 X |
| 4,528,183 | 7/1985 | Johnson | 424/195.1 X |
| 4,598,069 | 7/1986 | Hikino | 514/54 |
| 4,619,793 | 10/1986 | Lee | 264/2.6 |
| 4,634,449 | 1/1987 | Jenkins | 8/507 |
| 4,636,212 | 1/1987 | Posin | 623/6 |

FOREIGN PATENT DOCUMENTS 191520 2/1985 European Pat. Off. .

*Primary Examiner*—Matthew A. Thexton
*Assistant Examiner*—Catherine S. Kilby
*Attorney, Agent, or Firm*—Eric P. Schellin

[57] ABSTRACT

Method of using ophthalmic dosage of aqueous aloe vera gel as emollient and absorbent of UV radiation to shield eye retina by topically applying said gel in the eye.

11 Claims, No Drawings

OPHTHALMIC U.V. ABSORPTIVE EMOLLIENT

BACKGROUND OF THE INVENTION

Although ultra-violet radiation has long been recognized as a factor in the development of cutaneous cancer, aging of the skin, and mutagenic changes, it is only within the last decade or less that ultra-violet radiation has been universally recognized as a causative factor in ocular pathogenesis.

In humans, the eye has evolved into a sophisticated organ having neurophysiologic responses to photons in a certain portion of the electromagnetic spectrum, that provides a constant detailed map of the immediate environment. The action spectrum for these responses lie primarily within the 400-700 NM wavelength range, which has been labeled the visible spectrum or "Light".

The maximum of the eye's spectral response corresponds roughly to the maximum of solar spectral irradiance. Because solar UV radiation is present during most of the daylight hours, the eye may be exposed daily to some amount of solar ultraviolet radiation throughout life.

Wavelengths shorter than approximately 290NM or UV-C are partially or completely absorbed within the cornea and conjunctiva. The acute effects of exposure to these wavelengths are primarily those of conjunctivitis and a corneal inflammation reaction known as photokeratitis. The inflammatory reaction of the outermost layer of the eye to UV-C and UV-B radiation can be similar to that of the skin in some respects.

The clinical progress or picture of photokeratitis follows a characteristic course. For example, after exposure, there is a period of latency which varies somewhat inversely with the amount of exposure. The latent period may be as short as 30 minutes or as long as 24 hours but it is typically 6 to 12 hours.

Conjunctivitis, which is often accompained by an erythema of the skin surrounding the eyelids, is associated with the sensation of a foreign body or "sand" in the eyes, varying degrees of photophobia (intolerance to light), lacrimation (tearing), and blepharospasm (spasm of lid muscles). Corneal pain can be very severe, and the individual is usually incapacitated for some period of time. These acute symptoms usually last from 6 to 24 hours and almost all discomfort disappears within 48 hours. Very rarely does conjunctivitus causing exposure result in permanent damage.

However, unlike the skin, the ocular system does not develop tolerance to repeated ultraviolet exposure. Swelling or shrinking of groups of corneal epithelial cells leads to visibly recongizable stippling or irregular mosaic granulation of the corneal surface. With UV doses greater than the threshold for photokeratitis, surface epithelial cells show nuclear fragmentation, mid-epithelial cells show vacuole formation, and basel cells show inhibition of mitosis and clouding of the corneal stroma occurs. Inflammation is also present in the conjunctiva where vasodilation, edema, and inflammatory cell infiltrate is followed by desquamation.

When the cornea is damaged or replaced by surgery, the eye in general becomes very sensitive and the retina becomes vulnerable to ultra violet radiation below about 325 nm or in the UV-B and UV-C ranges. This is the opposite of what happens with a healthy or non-relaced cornea. In the healthy or undamaged eye, absorption of radiation by the cornea and lens of the human eye is such that very little radiation of wavelengths shorter than 390 NM reaches the retina.

The retina (tunica interna) is a delicate nervous membrane, upon which the images of external objects are received. Its outer surface is in contact with the choroid; its inner with the vitreous body. Behind, it is continuous with the optic nerve; it gradually diminishes in thickness from behind forward and extends nearly as far as the ciliary body, where it ends in a jagged margin, the ora serrata. Here the nervous tissues of the retina end, but a thin prolongation of the membrane extends forward over the back of the ciliary processes and iris, forming the pars ciliatis retinae and pars inidica retinae. This forward prolongation consists of the pigmentary layer of the retina together with a stratum of columnar epithelium. The retina is soft, semitransparent, and of a purple tint in the fresh state, owing to the presence of a coloring material named rhodopsin or visual purple; however, it soon becomes clouded, opaque, and bleached when exposed to sunlight. Prolonged exposure of the retina to UV-B and UV-C wavelengths causes damage to the retina.

SUMMARY OF THE INVENTION

Accordingly, it is a principal object of the present invention to provide a method for soothing the eye and protecting the retina of the eye from UV-B and UV-C radiations by delivering an ophthalmic chromophore dosage of an emollient gel into the eye, whereby prolonged retention of said chromophore is provided.

It is a further object of the invention to provide a method for soothing the mucous membranes of the eye and protecting the retina of the eye from UV-B and UV-C radiations after corneal transplants by delivering an ophthalmic chromophore dosage of an emollient gel into the eye, whereby prolonged retention of said chromophore is provided.

It is a yet further object of the invention to provide a method for soothing the mucous membranes of the eye and protecting the retina of the eye from UV-B and UV-C radiation by using a single gel as both an emollient and UV absorber or chromophore, as the sole dosage means to achieve prolonged retention of said emollient chromophore in the eye.

Another object further still is to provide a method for soothing the eye and protecting the retina of the eye from UV-B and UV-C radiation by using an aloe vera gel dispersion as both an emollient and UV absorber or chromophore as the sole dosage means to achieve prolonged retention of said emollient chromophore in the eye.

A still further object of the invention is to utilized ultra violet light plus aloe vera as a regimen for treatment of corneal ulcers.

These and other objects of the invention will become more apparent from the descriptions hereafter set further.

DETAILED DESCRIPTION OF THE INVENTION

U.S. Pat. No. 3,470,109 discloses a method of making reconstitutable aloe vera gel in dry crystalline form for use in the manufacture of pharmaceutical preparations; however, there has been no determination of the potential of the gel for use as liquid sunglasses applied topically in the eyes.

The cornea portion of the eye is considered to be a fat-water-fat sandwich. Chemical analysis shows the lipid content of the epithelium and endothelium to be 100 times greater than that of the corneal stroma. As a result, the epithelium and endothelium are relatively impermeable to electrolytes but are readily penetrated by fat-soluble substances.

The present invention discovery is that the differential solubility of penetration of the cornea is such that aloe vera gel is absorbed by the cornea fatty layer, and aloe vera gel can be used as an emollient ophthalmic chromophore dosage in the eye as an absorbent to prevent UV-B and UV-C radiation from reaching the retina.

While not wishing to be bound by a theory as to why or how said gel functions in this manner, it is worthy to note that the Merck Index indicates that the principal active ingredient of aloe is aloin which has the structure:

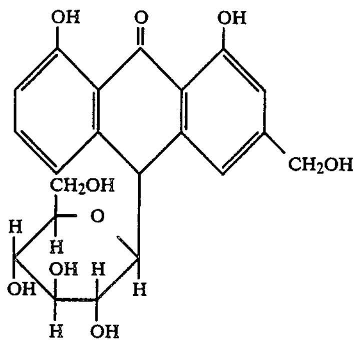

It is believed that when the aloe vera gel containing this active ingredient is topically placed in the eye, a UV-B and UV-C absorption spectrum equilibrium is established between the tear film and epithelium of the cornea of mammals.

Prolongation of the equilibrium appears to be accomplished by the viscous gel dispersion and/or a slow erosion of the viscous surface. The chromophore containing viscous or gel composition of aloe vera have a prolonged retention time in the eye and remain in contact with the surface of the eye for periods of from about 2 to about 4 hours.

The aloe vera gel can be used alone, or in admixture with a high molecular weight polymer which forms viscous gels. In this connection, polymers which can be used in the present invention have a molecular weight of from about 1 million to about 6 million, and are characterized by carboxylic or anhydride functional groups and preferably contains from 2 to 7 carbon atoms per functional group. The gels which form during the preparation of the aloe vera gel polymer dispersion have a viscosity of from about 40,000 to about 300,000 cps at 20 rmp (spindle 7) at 25° C. generated by an RVT Brookfield Viscometer, and preferably from about 75,000 to about 200,000 cps, most preferably from about 90,000 to about 150,000 cps.

Suitable polymers useful in the present invention are carboxypolymethylene, a carboxy vinyl polymer, (available under the trade name Carbopol from the B. F. Goodrich Company); and ethylene maleic anjydride, (available under the trade name EMA from the Monsanto Company).

When the aloe vera gel is used alone, a purified solution containing from 1% to 8% of the gel will suffice to provide liquid sunglasses which are absorbed by the cornea fatty layer to set up the UV-B and UV-C equilibrium between the tear film and the epithelium of the cornea.

In admixture with the high molecular weight polymers, the total weight of gel and polymer should still come up to between 4 to 6% by weight of the composition.

EXAMPLE I

The outer skin from leaves of the aloe vera plant are stripped-off to obtain the gel from the interior of the leaves. The gel is placed in a blender and mercerized from 3 to 5 minutes, and then filtered through a 60 mesh stainless steel screen. Purified water is then stirred into the gel to bring the gel contant to 4% by weight.

Thereafter, ophthalmic dosages of about 50 μL of the 4% gel are administered directly into the eyes of an albino rabbit, and the gel is active as a UV-B and UV-C absorber in the rabbit's eyes for a period of 2 to 4 hours.

EXAMPLE II

Aloe vera gel in the form of anydrous crystals is reconstituted by adding deionized water to restore the physical and chemical properties of the gel before it was lyophilized. When sufficient water has been added to make the gel about 6% by weight of the dispersion, the gel compositions contain about 94% by weight of water trapped in the matrix and is clear so that the vision is not blurred, because the gel refractive index is similar to that of tears.

Ophthalmic dosages of about 50 μl of the 6% gel are administered directly into the eyes of an albino rabbit and the gel is active as a UV-B and UV-C absorber in the rabbit's eyes for a period of 2 to 4 hours.

EXAMPLE III

A 3.8% by weight of ethylene maleic anhydride (available under the trade name of EMA -91 from Monsanto) solution in purified water is prepared and mixed using a high speed mixer with a 2% by weight dispersion of aloe vera gel in purified water.

Ophthalmic dosages of about 50 μl are administered directly into the eyes of an albino rabbit and the gel is active as a UV-B and UV-C absorber in the rabbit's eyes for a period of 2 to 4 hours.

Topically applied aloe vera chromophore gel emollient compositions of the invention, when placed in the eyes via drops, provide a film of UV-B and UV-C absorption spectrum equlibrium between the tear film and the epithelium of the cornea, and in addition to absorbing UV light which regular sun-glasses would absorb, the gel additionally absorbs the estimated 30 to 35% of UV-B and UV-C radiation that normally reaches the eyes from points above, below and from the sides of regular sun glasses.

In the context of the invention aloe vera gel alone, or together with the high molecular weight polymer can be used in the crystalline form and later reconstituted with purified water, prior to use as chromophore drops.

A method of preparing the crystalline form of aloe vera is disclosed in U.S. Pat. No. 3,470,109.

When utilizing aloe vera gel in crystalling form, deionized or distilled water is added in the aloe vera gel in crystalling form, to obtain reconstituted aloe vera gel having the same physical properties and chemical properties of the aloe vera gel before it was lyophilized. By the amount of water added, the viscosity and other features of the aloe vera gel may be controlled. In general, a viscosity in the range of about 40,000 to about 300,000 cps will suffice, more preferably from about 75,000 to about 200,000 cps, and most preferably from about 90,000 to about 150,000 cps.

The germicidal properties of ultra violet light are well known and widely used for sterilization, and in view of the resistence of many viruses, fungi and bacteria to antibiotics, the invention utilizes a combination of ultra violet light treatment and aloe vera to treat corneal ulcers Peak germicidal activity occurs at a wavelength of about 265 nm (most effective wavelength against viruses and fungi as well as against bacteria), and nucleoprotein absorption of UV light has a similar peak. In view of this fact, it is believed that the germicidal effect is a result of nucleo protein destruction.

For reasons not fully clear some actinic keratitis is produced most effectively at a wavelength of 288 nm.

However the invention discovery is that superimposition of the germicidal and keratitis producing spectral curves indicate that, at about 253.7 nm the germicidal effect is 85% of maximum, whereas the keratitis effect is only 20% of maximum.

Utilizing this fact, a low pressure mercury vapor lamp calibrated at about 253.7 nm is used to expose the eyes of an albino rabbit held in the open position to radiation for 30 seconds. During this time, the lamp is held approximately 5 mm away from the cornea.

The exposed cornea is then treated by delivering an ophthalmic chromophore emollient gel of aloe vera to the surface of the eye to establish a UV absorption spectrum equilibrium between the tear film epithelium of the cornea. This post treatment is an important step because UV radiation effects are accumulative, and the cornea must be protected for a period of from about 5 to about 10 days from atmospheric and environmental UV in the UV-C and UV-B ranges. After about 5 to 7 days after the post treatment step, the epithelium of the cornea is normally replaced by normal growth processes.

The length of time the rabbit's eye is exposed to radiation will depend upon the kin and types of viruses, fungi and bacteria present, however, it has been found that an exposure period of from about 30 to 300 seconds will suffice in the context of the invention. While the preferred wavelength is 253.7 nm, it has been found that wavelengths±50 nm from this value is operable in the invention context.

What is claimed is:

1. An ophthalmic aqueous gel for preventing UV-B and UV-C radiation from reaching the eye retina upon placement in the eye to establish a UV absorption spectrum equilibrium between the tear film and epithelium of the cornea of the eye, said gel comprising an aloe vera chromophore emollient gel present in amounts of from about 1% to about 8% by weight in said ophthalmic aqueous gel.

2. An ophthalmic aqueous gel for preventing UV-B and UV-C radiation from reaching the eye retina upon placement in the eye to establish a UV absorption spectrum equilibrium between the tear film and epithelium of the cornea of the eye, said gel comprising an aloe vera chromophore emollient gel and a gel-forming ethylene maleic anhydride polymer having a molecular weight in excess of 1,000,000, wherein the combined weights of chromophore and polymer are from 4 to 6 percent by weight of said ophthalmic aqueous gel; said ophthalmic gel having a viscosity of from about 40,000 to about 300,000 cps.

3. An aqueous gel in accordance with claim 2 wherein said polymer has a molecular weight from about 1,000,000 to about 6,000,000.

4. An aqueous gel in accordance with claim 2 wherein said gel has a viscosity of from about 75,000 to about 200,000 cps.

5. An aqueous gel in accordance with claim 2 wherein said gel has a viscosity of from about 90,000 to about 150,000 cps.

6. A method for delivering an ophthalmic chromophore gel to the surface of the eye to prevent UV-B and UV-C radiation from reaching the eye retina by establishing a UV adsorption spectrum equilibrium between the tear film and epithelium of the cornea over extended periods of time, comprising adding to purified water aloe vera gel in an amount of 4 to 6% by weight of said opthalmic gel and introducing said ophthalmic gel into the eye.

7. The method of claim 6 wherein said gel further includes a gel-forming high molecular weight ethylene maleic anhydride polymer having a molecular weight in excess of 1,000,000 and said gel has a viscosity of between about 40,000 and about 300,000 cps.

8. A method in accordance with claim 7 wherein said polymer has a molecular weight of from about 1,000,000 to about 6,000,000.

9. A method in accordance with claim 7 wherein said aqueous gel has a viscosity of from about 75,000 to about 200,000 cps.

10. A method in accordance with claim 7 wherein said gel has a viscosity of from about 90,000 to about 150,000 cps.

11. A method of treating corneal ulcers comprising exposing the eye of a subject of to U.V. radiation in the range of from about 203.7 to about 303.7 nm for a period of from about 30 to 300 seconds, and delivering an ophthalmic chromophore emollient gel to surface of the eye to establish a U.V. absorption spectrum equilibrium between the tear film and epithelium of the cornea; said gel is selected from the group consisting of aloe vera aloe or in admixture with a gel-forming ethylene maleic anhydride polymer having a molecular weight in excess of 1,000,000.

* * * * *